United States Patent [19]

Kunstle et al.

[11] 3,960,909

[45] June 1, 1976

[54] PROCESS FOR PREPARING PALLADIUM(II)ACETYLACETONATE

[75] Inventors: Gerhard Kunstle, Raitenhaslach; Herbert Siegl, Haiming, both of Germany

[73] Assignee: Wacker-Chemie GmbH, Munich, Germany

[22] Filed: Jan. 7, 1975

[21] Appl. No.: 539,123

[30] Foreign Application Priority Data

Jan. 18, 1974 Germany............................ 2402383

[52] U.S. Cl............................. 260/429 J; 260/429 R
[51] Int. Cl.² ......................................... C07F 15/08
[58] Field of Search ...................... 260/429 J, 429 R

[56] References Cited
UNITED STATES PATENTS

| | | | |
|---|---|---|---|
| 3,474,464 | 10/1969 | Matthews et al................ | 260/429 R |
| 3,705,163 | 12/1972 | Howitz et al................. | 260/429 J X |
| 3,787,462 | 1/1974 | Swodenk et al.................. | 260/429 J |
| 3,876,675 | 4/1975 | Trofimenko .................... | 260/429 J |

OTHER PUBLICATIONS

Chemical Abstracts, vol. 8, p. 2988 (1914).
Chemical Abstracts, vol. 52, 152d (1958).
Chemical Abstracts, 65, 8318g (1966).
Chemical Abstracts, 73, 76663w (1970).
Chemical Abstracts, 47, 11060g (1953).

*Primary Examiner*—Helen M. S. Sneed
*Attorney, Agent, or Firm*—Allison C. Collard

[57] ABSTRACT

A process for preparing palladium(II)acetylacetonate having a low content in organically linked chlorine by reaction of acetylacetone with palladium dichloride or the complex tetrachloropalladinates derived therefrom, which comprises dissolving the starting palladium dichloride compound in hydrochloric acid, adding to the solution at least the stoichiometric amount of acetylacetone, stirring until the solution has become clear, adjusting the solution to a pH-value between 7 and 8 by drop-wise addition of an aqueous alkali hydroxide solution, separating the precipitated palladium(II)acetylacetonate from the solution, rinsing the palladium(II)acetylacetonate with water to free it from inorganic chloride, and drying. The products made by the process of the invention are effective catalysts in a variety of synthetic processes e.g. oxosyntheses, oligo and polymerizations, vinylization of aromatics and so on.

6 Claims, No Drawings

PROCESS FOR PREPARING PALLADIUM(II)ACETYLACETONATE

The present invention relates to a process for preparing palladium(II)acetylacetonate with a low content of organically linked chlorine, from palladium chloride or complex tetrachloropalladinates and acetone.

Palladium and its salts have been used for quite some time in a large variety of organic reactions. They are e.g. used in hydrogenations, in oxidations for the production of ketones, aldhydes, and esters from olefins, and, provided the required palladium compound is soluble in non-polar hydrocarbons, in homogeneous solvent polymerizations of unsaturated aliphatic hydrocarbons. It is also a fact that metal acetylacetonates have been successfully used as catalysts in many chemical processes ranging from polymerizations, over oxidations, hydrogenations, oxo-sytheses, esterifications and trans-esterifications to a large number of special reactions. Palladium(II)acetylacetonate is therefore of particular importance in the field of catalytical reactions on a large scale.

In a Russian publication (see A. A. Grinberg, L. K. Simonova, Journal Appl. Chem. USSR 26, page 801, 1953) the preparation of palladium(II)acetylacetonate from chlorine-containing compounds is described. The end product, however, contains a large amount of organically linked chlorine, whereby the catalytical effectiveness is considerably decreased, since chlorine ions counteract the reaction.

In a process described in DAS No. 1,904,235, a water insoluble palladium compound is precipitated from an alkali palladium chloride solution by means of alkali hydroxide solution, the palladium compound being then converted into palladium(II)acetylacetonate with acetylacetone. While the chlorine content of the end product in that case is below 0.05% by weight, the disadvantage inherent in the process is that the water insoluble intermediate palladium compound may be contained in the end product, which is also water insoluble; however, for catalytical purposes a very high degree of purity is required from the palladium(II)acetylacetonate.

It is therefore the object of the present invention to provide a process for preparing palladium(II)acetylacetonate with a very low content of organically linked chlorine.

It is another object of the invention to provide a process which leads directly in one operation to a pure palladium(II)acetylacetonate with elimination of time consuming and yield reducing intermediate steps.

The process for preparing palladium(II)acetylacetonate according to the invention, which is low in organically linked chlorine, is comparatively simple. Palladium dichloride or complex tetrachloropalladinates derived therefrom are dissolved in hydrochloric acid and thereto is added at least the stoichiometric amount of acetylacetone and the mixture is stirred until a clear solution results. Then a pH-value of 7 to 8 is adjusted by adding an aqueous alkali hydroxide solution drop by drop; the precipitated palladium(II)acetylacetonate is separated, and inorganic chloride is washed out with water and dried. The reaction is carried out in practice at a temperature ranging from 5° to 100°C, and preferably 15°–35°C. In carrying out the process, palladium dichloride or a complex tetrachloropalladinate, for instance, alkali-tetrachloropalladinate $Na_2PdCl_4$ or $K_2PdCl_4$ is dissolved in 1½ to 2½ times the amount of hot concentrated hydrochloric acid. The solution, if necessary, is somewhat concentrated, cooled down and diluted with water to five–ten times, preferably six to eight times, its volume.

Subsequently, an at least stoichiometric amount, preferably a 5 molar to 10 molar % excess of acetylacetone is added and stirring is carried out until the solution is clear. Only then, a pH-value of 7 to 8 is adjusted by dropwise addition of an aqueous alkalihydroxide solution, preferably of 3N–5N.

The precipitated palladium(II)acetylacetonate can be easily filtered or centrifuged. Thereafter, inorganic chloride is rinsed out by water, so that only a residual chlorine content remains which consists of organically linked chlorine.

The moist product is then dried at a temperature of 20°–80°C, preferably 40°–60°C at reduced pressure, preferably 5–30 torr. The dried palladium(II)acetylacetonate has a water content of less than 0.1% by weight and is soluble in benzene at a rate of more than 99% by weight. Beginning at 190°C, decomposition of the product sets in. Of course, there are other methods of drying available, such as pouring onto absorptive paper, withdrawal of solvent in a rotary evaporator, and the like.

The palladium(II)acetylacetonate made according to the invention is obtained in a high yield, analytically pure, and is almost completely free of chlorine. It can be directly used as catalyst for oxo-syntheses, e.g. allyl alcohol or methacrylic acid from propylene, for dimerizations, oligomerizations, polymerizations, such as ethylene to 1.3-butadiene, in the vinylization of aromatics, e.g. benzene with vinyl acetate to 2-phenylvinyl acetate, and in the alkine addition to aromatics, e.g. preparation of styrene.

In the following, the invention will be more fully described in a specific example, which is given by way of illustration and not of limitation.

EXAMPLE 15 grams palladium chloride were dissolved in 25 ml of hot concentrated hydrochloric acid, and after cooling down, diluted with 170 ml water. After the addition of 17.75 grams acetyl acetone, the solution was stirred for 15 minutes until it was clear. Thereafter, a pH of 7.5 was adjusted by dropwise addition of 4 N sodium hydroxide solution at room temperature. The precipitated palladium(II)acetylacetonate was filtered off, washed to free it of chloride with about 1 liter of water, and dried at 50°C at 10 torr.

The yield was 25.5 grams corresponding to 99% of the theoretical. The palladium(II)acetylacetonate obtained was canary yellow and finely crystalline, with a Cl content of 0.008% and less than 0.1% water.

Analysis: Calculated: C, 39.42; H, 4.63; Pd, 34.94.
Found: C, 39.47; H, 4.88; Pd, 34.64.
Melting point beginning at 190°C while decomposing.

What is claimed is:

1. A process for preparing palladium(II)acetylacetonate having a low content in organically linked chlorine by reaction of acetylacetone with palladium dichloride or an alkalitetrachloropalladinate selected from the group consisting of potassium and sodium tetrachloropalladinate, which comprises dissolving the starting palladium compound in 1½ to 2½ times the amount by weight of concentrated hydrochloric acid, adding to the solution at least the stoichiometric amount and up to 10 molar % of acetylacetone, stirring until the solution has become clear, adjusting the solution to a pH value between 7 and 8 by drop-wise addition of an aqueous alkalihydroxide solution, separating the precipitated palladium(II)-acetylacetonate from the solution, rinsing with water to free the precipitate from inorganic chloride, and drying.

2. The process according to claim 1, wherein the reaction is carried out at a temperature between 5° and 100°C.

3. The process according to claim 2, wherein the reaction is carried out at a temperature between 15° and 35°C.

4. The process according to claim 1, wherein an excess amount of acetylacetone of preferably 5–10 molar % is used in the reaction.

5. The process according to claim 1, wherein the separated palladium acetyl-acetonate is dried at a temperature of 20°–80°C.

6. The process according to claim 5, wherein the drying is carried out at 40°–60°C and at a pressure of 5–30 torr.

* * * * *